(12) United States Patent
Dai et al.

(10) Patent No.: US 10,418,928 B2
(45) Date of Patent: Sep. 17, 2019

(54) ADJUSTABLE CIRCUIT FOR PERSONAL ELECTRIC CLEANING CARE APPLIANCE

(71) Applicant: SHANGHAI SHIFT ELECTRICS CO., LTD., Shanghai (CN)

(72) Inventors: Xiaoguo Dai, Shanghai (CN); Zhenwu Xu, Shanghai (CN); Ling Dai, Shanghai (CN)

(73) Assignee: SHANGHAI SHIFT ELECTRICS CO., LTD., Shanghai (CN)

( * ) Notice: Subject to any disclaimer, the term of this patent is extended or adjusted under 35 U.S.C. 154(b) by 34 days.

(21) Appl. No.: 15/771,725

(22) PCT Filed: Oct. 29, 2015

(86) PCT No.: PCT/CN2015/093181
§ 371 (c)(1),
(2) Date: Apr. 27, 2018

(87) PCT Pub. No.: WO2017/070887
PCT Pub. Date: May 4, 2017

(65) Prior Publication Data
US 2019/0068100 A1    Feb. 28, 2019

(51) Int. Cl.
*B65G 27/32* (2006.01)
*H02P 25/034* (2016.01)
(Continued)

(52) U.S. Cl.
CPC .......... *H02P 25/034* (2016.02); *A61C 17/221* (2013.01); *A61C 17/34* (2013.01); *H02P 25/032* (2016.02); *H02P 25/06* (2013.01)

(58) Field of Classification Search
CPC ........ B65G 27/32; H02P 25/034; H02K 33/02
See application file for complete search history.

(56) References Cited

U.S. PATENT DOCUMENTS

| 4,331,263 A * | 5/1982 | Brown ............... B65G 27/32 198/751 |
| 5,189,751 A | 3/1993 | Giuliani et al. |

(Continued)

FOREIGN PATENT DOCUMENTS

| CN | 104617704 A | 5/2015 |
| CN | 104617732 A | 5/2015 |

(Continued)

OTHER PUBLICATIONS

European Patent Application No. 15906953.3; Search Report; dated Sep. 26, 2018; 4 pages.

(Continued)

*Primary Examiner* — Bickey Dhakal
*Assistant Examiner* — Cortez M Cook
(74) *Attorney, Agent, or Firm* — BakerHostetler

(57) ABSTRACT

An adjustable circuit for a personal electric cleaning care appliance comprises comprising a power supply portion and a driver is disclosed. The driver comprises a transducer, a drive coil and an iron core of the drive coil, and a drive shaft of the transducer is equipped with cleaning elements. The adjustable circuit comprises a microchip processor and an H-bridge drive circuit. By connecting a capacitor bank and the drive coil in series at load ends of the H-bridge drive circuit, at least a part of the capacitors of the capacitor bank is controllably connected in series with the drive coil or disconnected from the drive coil, the capacitance of the connected capacitor can be controlled so that the current flowing through the drive coil is controllably limited to a certain value, thereby, the motion amplitude of the cleaning elements can be controlled, and no additional electromagnetic interference will occur.

3 Claims, 9 Drawing Sheets

(51) Int. Cl.
*H02K 33/02* (2006.01)
*H02P 25/06* (2016.01)
*H02P 25/032* (2016.01)
*A61C 17/22* (2006.01)
*A61C 17/34* (2006.01)

(56) References Cited

U.S. PATENT DOCUMENTS

| | | |
|---|---|---|
| 6,002,256 A | 12/1999 | Slade |
| 2007/0011834 A1 | 1/2007 | Shimizu et al. |
| 2009/0046482 A1 | 2/2009 | Smith |

FOREIGN PATENT DOCUMENTS

| | | |
|---|---|---|
| CN | 104868608 A | 8/2015 |
| CN | 105227036 A | 1/2016 |
| CN | 205160423 U | 4/2016 |
| WO | WO 2008/053441 A1 | 5/2008 |

OTHER PUBLICATIONS

European Patent Application No. 15906953.3; Office Action—Article 94(3); dated Oct. 12, 2018; 9 pages.
International Patent Application No. PCT/CN2015/093181; Int'l Search Report; dated Jul. 1, 2016; 2 pages.

\* cited by examiner

ADJUSTABLE CIRCUIT FOR PERSONAL ELECTRIC CLEANING CARE APPLIANCE

CROSS-REFERENCE TO RELATED APPLICATIONS

This application is the national stage of International Application No. PCT/CN2015/093181 filed Oct. 29, 2015. The entirety of which are incorporated herein by reference.

TECHNICAL FIELD

The present invention relates to an adjustable circuit for a personal electric cleaning care appliance, and more specifically, to a circuit with adjustable electrical efficiency and amplitude for a personal electric cleaning care appliance.

BACKGROUND

In a personal electric cleaning care appliance (hereinafter referred as cleaning care appliance), a resonance oscillation driving system is frequently used to drive the cleaning care appliance for a rotary motion. As described in the applicant's another patent application PCT/CN2015/071696, the cleaning care appliance comprises a handle with a handle housing. The handle housing is equipped internally with a power supply portion for supplying power to various parts of the cleaning care appliance, a control portion for controlling various operation modes of the cleaning care appliance and turning on or off of the cleaning care appliance, a trigger portion for turning on or off the operation of the cleaning care appliance, and a driver for converting the input electrical energy into mechanical energy output. The driver comprises a transducer, a drive coil, and an iron core of the drive coil located in the drive coil.

FIG. 1 is a schematic diagram of an existing driver. As shown in FIG. 1, when an alternating current i flows through the drive coil, the permanent magnets distributed on the transducer are subjected to a reaction force of the electromagnetic force to drive the transducer to make a reciprocating rotary motion at the frequency of the alternating current, so as to bring the cleaning element carrier and the cleaning elements assembled on the drive shaft of the transducer to perform a reciprocating rotary motion, thus obtaining a cleaning effect. In the above structure, the transducer, the cleaning element carrier and the cleaning elements have natural frequency $f_n$, and the current in the drive coil has its driving frequency $f_0$. The $f_n$ is very close to the $f_0$. Generally, if the condition $0.85f_0<f_n<1.05f_0$ is satisfied, the electromagnetic force between the drive coil and the transducer could enables the transducer, the cleaning element carrier and the cleaning elements to be in a resonance oscillation state, as a result, a higher mechanical efficiency can be achieved.

An actuator system of the resonance oscillation utilizing magnetic effect for an electric toothbrush is disclosed in the invention patent application of publication NO. CN 103140190 A, which comprises an induction windings located adjacent to the coil windings, the motion of the permanent magnet component generates magnetic flux which induces a voltage in the induction windings according to the position of the induction coils with respect to the permanent magnets. Such an actuator system further comprises a control component, the control component is used to process voltage signals from the induction windings to resolve the voltage generated only by the magnetic flux from the permanent magnet component and is used to compare the voltage with a standard value, and then the comparison value is used to change the frequency or duty cycle of the driving signal, so that the spindle stroke has the desirable magnitude and/or angle. However, neither of these two disclosed documents relates to the specific structure of the circuit, the control mode, and problems such as how to improve the circuit efficiency.

In existing personal electric cleaning care appliances, the electrical energy is converted into mechanical energy by means of the drive coil. To improve cleaning effects, the cleaning elements are usually required to possess rotary motions of different motion amplitudes, so as to meet different requirements of the user. In one prior art, by regulating the current frequency of the drive coil, the frequency of the electromagnetic force between the drive coil and the transducer is made even far away from the natural frequency of the transducer, the cleaning element carrier and the cleaning elements, thus reducing the amplitude of the rotary motion of the cleaning elements. However, this method increases the current of the drive coil, so that the overall power consumption of the cleaning care appliance is increased and the output mechanical power becomes lower. In another prior art, the mean current flowing through the drive coil is decreased by controlling the time during which the current flows through the drive coil, for example, the current in the drive coil is frequently switched using a PWM (pulse-width modulation) mode. The smaller mean current in the drive coil can reduce the motion amplitude of the cleaning elements. This method can obtain a smaller motion amplitude of the cleaning elements while reducing the overall power consumption, however, frequently on-off of the current in the drive coil may cause electromagnetic interference and thus pollution of the environment. It is certainly that an electromagnetic interference can be shielded by other means, but it will increase the cost.

SUMMARY

The object of the present invention is to provide a high-efficiency circuit with adjustable electrical efficiency for the personal electric cleaning care appliance, so that the volume and manufacturing cost of the cleaning care appliance are not increased. Another object of the present invention is to optimize the electrical phase angle of the current in the drive coil and the terminal voltages of the drive coil, so as to adjust the electrical efficiency of the drive coil and to adjust the motion amplitude of the cleaning elements.

It is know that a personal electric cleaning care appliance comprises a power supply portion for supplying power to various parts of the cleaning care appliance, a control portion for controlling various operation modes of the cleaning care appliance, a trigger portion for turning on or off the operation of the cleaning care appliance, and a driver for converting the input electrical energy into a mechanical energy output. The power supply portion comprises an H-bridge drive circuit composed of transistors. The driver comprises a transducer, a drive coil and an iron core of the drive coil located within the drive coil. The transducer is provided with an elastic element and permanent magnets thereon, and the drive shaft of the transducer is equipped with a cleaning element carrier and cleaning elements. According to the present invention, the provided adjustable circuit for a personal electric cleaning care appliance comprises a microchip processor IC and the H-bridge drive circuit, assuming that the driving frequency generated by the H-bridge drive circuit is $f_0$, when an alternating current i is fed through the drive coil, the current in the drive coil contains a sinusoid current part with a frequency $f_0$, the cleaning elements, the cleaning element carrier and the transducer make a reciprocating rotary motion in a resonance oscillation mode under the action of the electromagnetic force with a setting frequency $f_0$ generated by the drive coil, the cleaning elements, the cleaning element carrier and the transducer have a natural frequency $f_n$, in such a way that $f_n$ satisfies $0.85f_0 < f_n < 1.05f_0$. During a certain subdivision time period of the operation of the electric cleaning care appliance corresponding to an operating mode, the current in the drive coil has a unique constant frequency; wherein a capacitor bank and a drive coil in series with the capacitor bank are connected at load ends of the H-bridge drive circuit, and at least a part of the capacitors of the capacitor bank is controlled to be in series with the drive coil or be disconnected with the drive coil through an interface I/O of the programmable microchip processor IC, as a result, the capacitance of the connected capacitor(s) can be controlled so that the current flowing through the drive coil is controllably limited to a value between approximate zero to $$\frac{\frac{4}{\pi}U_0}{R_L + ZNBl^2}$$

in order to control the size of amplitude of the motion of the cleaning elements, where $U_0$ is the output voltage of the power supply, $R_L$ is the DC resistance of the drive coil, Z is the change rate of the amplitude of the velocity component of the permanent magnets perpendicular to the direction of the magnetic lines with respect to the amplitude of the current of the drive coil, Z is obtained experimentally, N is the number of turns of the drive coil cut by the magnetic lines, B is the magnetic field density at the drive coil conductor, l is the effective length of the coil conductor cut by the magnetic lines; wherein the capacitor bank comprises a plurality of capacitors ($C_{72}$, $C_{73}$, ... $C_{7(n-3)}$) which are connected in series with corresponding transistors ($Q_{75}$, $Q_{76}$, ... $Q_{7n}$) respectively to form branches, these branches are connected in parallel with each other and in series with the drive coil, during a positive half cycle or a negative half cycle or a whole cycle of the current of the drive coil, the transistor (Q) and the drive coil in at least one branch are kept always turned on or off synchronously.

The equivalent capacitance value of the capacitor bank may be selected, so that the loop resistance of the drive coil and the capacitor bank is purely resistive.

The capacitor bank may further comprise a plurality of capacitors which are connected in series with a corresponding transistor respectively to form branches. These branches are connected in parallel with each other and in series with the drive coil, wherein, during the positive half cycle or the negative half cycle or the whole cycle of the current of the drive coil, the transistor(s) and the drive coil in at least one branch are kept always on or off synchronously.

The capacitor bank may also comprise at least two capacitors in parallel with each other.

Due to that capacitor bank and the drive coil connected in series with the capacitor bank, which can control the capacitance in real time, are connected at the load ends of the H-bridge drive circuit, the power factor cos φ of the circuit is controlled by controlling the equivalent capacitance of the connected capacitor bank, the size of the current in the drive coil can be controlled and thus the size of the rotation amplitude of the cleaning elements is controlled, whereby, a smaller motion amplitude of the cleaning elements is achieved at a lower power consumption, and no additional electromagnetic interference will occur. Especially, when the current in the drive coil has a unique constant frequency during a certain subdivision time period of the operation of the electric cleaning care appliance corresponding to an operation mode, the electric power efficiency of the drive coil can be the highest.

Figure 1:
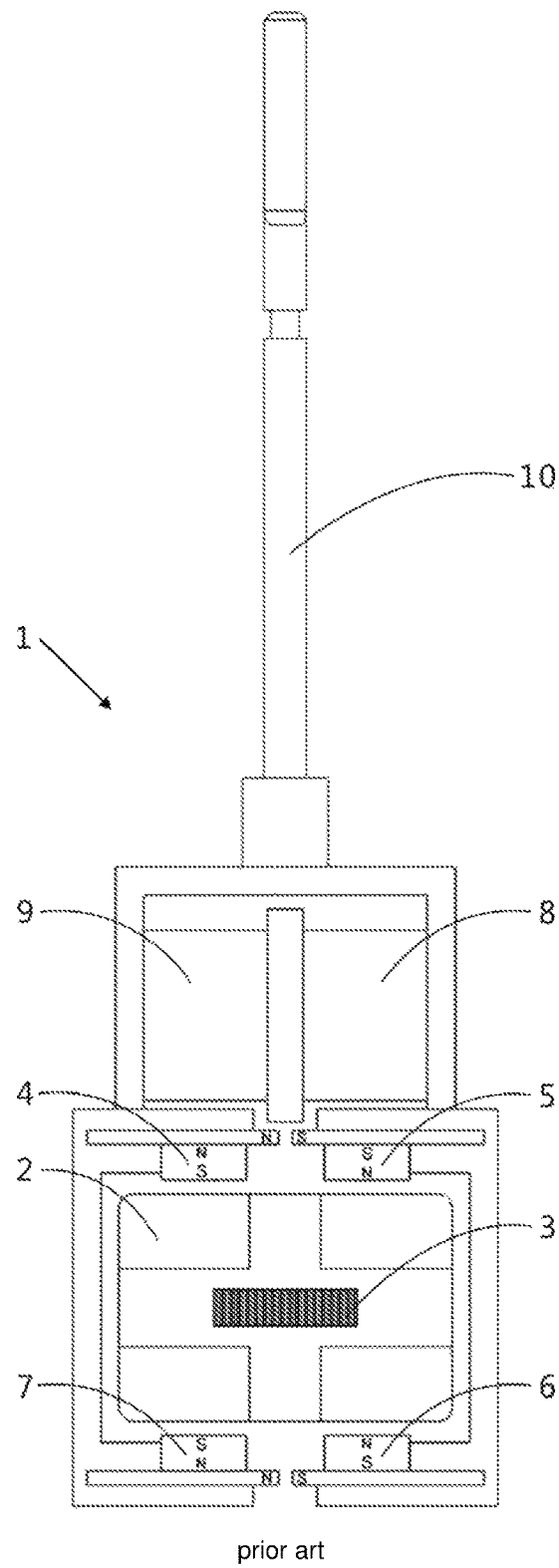
FIG. 1 is a schematic diagram of an existing driver.

EXPLANATION OF MAIN REFERENCE NUMERALS 1 driver
2 drive coil
3 iron core of the drive coil
4, 5, 6, 7 permanent magnets of the transducer
8, 9 elastic elements of the transducer
10 drive shaft of cleaning elements in the transducer
A one input node of the drive coil
$B_0$ another input node of the drive coil
D load node of the H-bridge drive circuit
E load node of the H-bridge drive circuit
$H_0$ high level output at the I/O interface
$U_0$ output voltage of the power supply
R . . . resistor
Q . . . transistor
IC programmable microchip processor
I/O . . . different input/output interface of IC
C capacitor
$R_L$ DC resistance of the drive coil
L ideal inductance without internal resistance corresponding to the drive coil
ω electrical angular speed t time
f₀ driving frequency
i current passing through the drive coil
I amplitude of current passing through the drive coil
l effective length of the coil conductor cut by magnetic lines
N the number of turns of the drive coil cut by magnetic lines
B magnetic field density at the drive coil conductor
υ velocity component of the permanent magnets in the direction perpendicular to magnetic lines
$υ_M$ amplitude of velocity component of the permanent magnets in the direction perpendicular to magnetic lines

DETAILED DESCRIPTION

Hereinafter, an exemplary embodiment of the present invention will be described in more detail taking an electric toothbrush as a typical example of the personal electric cleaning care appliance of the present invention while referring to the attached drawings. Although the electric toothbrush is used below as an example for explanation, the present invention is not limited thereto. The present invention is also applicable to personal electric cleaning care appliances such as an electric shaver, an electric cleanser, an electric shower and the like.

As stated above, a resonance oscillation driving system is often used in the personal electric cleaning care appliance to drive the cleaning care appliance to perform reciprocating rotary motion.

In the present invention, a driver circuit of the resonance oscillation for the personal electric cleaning care appliance comprises a power supply portion, a control portion and a trigger portion. The power supply portion supplies electric power to various parts of the cleaning care appliance; the control portion is used to control various operation modes of the cleaning care appliance; and the trigger portion is used to turn on or off the operation of the cleaning care appliance. The power supply portion is a DC power supply, which can be composed of a plurality of rechargeable batteries or a plurality of dry batteries. The power supply portion may also contain a well-known H-bridge drive circuit composed of transistors and capable of enabling positive and negative current pass through the loads. The driving frequency generated by the H-bridge drive circuit is set to be $f_0$. When an alternating current passes through the drive coil, the current in the drive coil contains a sinusoid current part with a frequency $f_0$.

Figure 2:
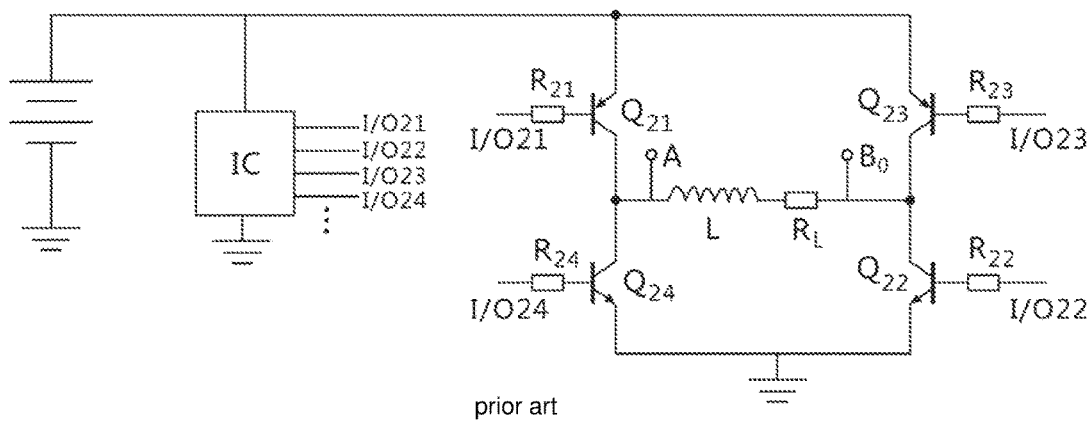
FIG. 2 is an existing control circuitry.
Figure 3:
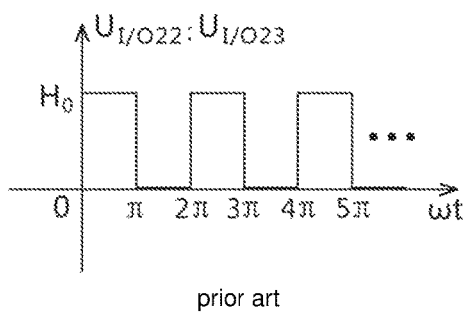
FIG. 3 is a voltage timing diagram of I/O22, I/O23 in the circuit IC as shown in FIG. 2.
Figure 4:
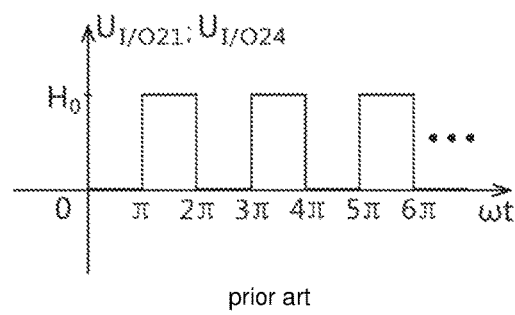
FIG. 4 is a voltage timing diagram of I/O21, I/O24 in the circuit IC as shown in FIG. 2.
Figure 5:
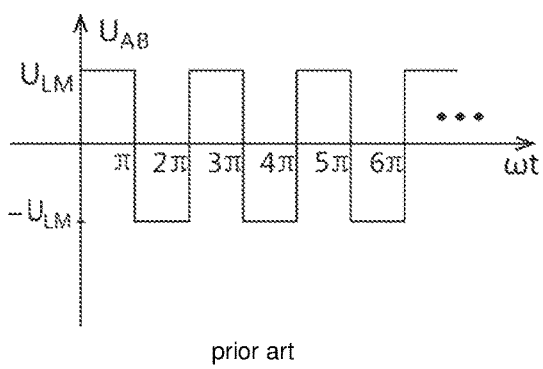
FIG. 5 is a timing diagram of the voltage at the two terminals of the drive coil corresponding to the output at the I/O interface in the circuit IC as shown in FIG. 2.

FIG. 2 presents an existing typical H-bridge drive circuit using a battery as the DC power supply for generating an alternating current with a frequency $f_0$ on the drive coil. When the microchip processor IC controls I/O21, I/O22, I/O23, I/O24 to output voltage signals according to the voltage timing sequence shown in FIGS. 3 and 4, the transistors $Q_{21}$, $Q_{22}$ and the transistors $Q_{23}$, $Q_{24}$ turn on alternately, positive and reverse currents flow through the drive coil alternately, and the voltage timing diagram on the drive coil approximates that as shown in FIG. 5. As is well known, the electrical angular speed $\omega=2\pi f_0$, where $f_0$ is a driving voltage or current frequency. As can be seen from FIG. 5, in the circuit shown in FIG. 2, a rectangular wave voltage with a frequency $f_0$ is generated on the drive coil.

$$U_{AB_0} = \begin{cases} U_{LM} (2n-2)\pi \leq \omega t < (2n-1)\pi & (n=1,2,3,\dots) \\ -U_{LM} (2n-1)\pi \leq \omega t < 2n\pi & (n=1,2,3,\dots) \end{cases} \quad (1)$$

Expanding it according to Fourier series, $$U_{AB_0} = \frac{4}{\pi} U_{LM} \left[ \sin\omega t + \frac{1}{3}\sin3\omega t + \frac{1}{5}\sin5\omega t + \dots + \frac{1}{2m-1}\sin(2m-1)\omega t + \dots \right] \quad (2)$$

$(\omega t \in R, \omega t \neq k\pi, k \in z, m \in N_+)$

Where $U_{AB_0}$, is a voltage across the two terminals A and $B_0$, $U_{LM}$ is a amplitude of DC voltage at the drive coil, m is the order of the higher-order harmonics, ω is the electrical angular speed, and t is the time.

That is to say, the rectangular wave with a driving frequency $f_0$ as shown in FIG. 5 can be decomposed into an infinite number of sinusoidal waves with different amplitudes and different frequencies. Apparently, the fundamental wave $$\frac{4}{\pi} U_{LM} \sin\omega t$$

has the maximal amplitude, the amplitude of the third harmonic is ⅓ of the amplitude of the fundamental wave, the amplitude of the fifth harmonic is ⅕ of the amplitude of the fundamental wave, and it's know from the terminal voltage equation of the drive coil that:

$$U_L = iR_L + NBl\upsilon + j\omega Li \quad (3)$$

$U_L$ comprises a real part ($iR_L+NBl\upsilon$) and an imaginary part ($j\omega Li$), The dimension of the real part is $iR_L+NBl\upsilon$, and the dimension of the imaginary part is $\omega Li$, $$i = \frac{U_L - NBl\upsilon}{R_L + j\omega L} \quad (4)$$

$$NBl\upsilon = U_L - (iR_L + j\omega Li) \quad (5)$$

where $U_L$ is the terminal voltage of the drive coil, $R_L$ is the DC resistance of the drive coil, N is the number of turns of the drive coil cut by magnetic lines, B is the magnetic field density at the drive coil conductor, l is the effective length of the coil conductor cut by magnetic lines, υ is the velocity component of the permanent magnets in the direction perpendicular to magnetic lines, L is the ideal inductance without internal resistance corresponding to the drive coil, i is the current flowing through the drive coil, and w is the electrical angular speed.

The transistor Q in the present invention can be a unipolar transistor, and it also can be a bipolar transistor. In the following embodiments, the bipolar transistor is used as an example for analysis and explanation, its analysis results are also suitable for a unipolar transistor.

In the present invention, the transducer is provided therein with elastic elements and permanent magnets which are driven by the reaction force of the electromagnetic force. The transducer, the cleaning element carrier and the cleaning elements constitute one vibrating body conforming to the simple harmonic vibration law. According to the principle of simple harmonic vibration, when the function of the reaction force subjected by the permanent magnets of the transducer due to the electromagnetic force with a frequency $f_0$ with respect to $\omega t(2\pi f_0 t)$ is a sine or cosine function, the function of the displacement and velocity at which the permanent magnets of the transducer make reciprocating rotary motion with respect to $\omega t(2\pi f_0 t)$ is also a sine or cosine function. Still further, when the natural frequency $f_n$ of the rotary motion of the transducer, the cleaning element carrier and the cleaning elements is equal to the frequency $f_0$ of the reaction force of the electromagnetic force, the transducer, the cleaning element carrier and the cleaning elements are in a resonant vibration state under the driving of the reaction force of the electromagnetic force. By this time, when the permanent magnets of the transducer make a reciprocating rotary motion, the direction of the velocity component of the permanent magnets in the direction perpendicular to the magnetic lines is identical to the direction of the reaction force of the electromagnetic force, that is, the electrical angle difference therebetween is zero.

The rotary motion of the transducer, the cleaning element carrier and the cleaning elements has a natural frequency $f_n$, the current in the drive coil has a driving frequency $f_0$. By bringing $f_n$ and $f_0$ very close to each other in the present invention, for example, to make them satisfy the inequality $0.85f_0 < f_n < 1.05f_0$, the electromagnetic force between the drive coil and the transducer could cause the transducer, the cleaning element carrier and the cleaning elements to be in a resonance oscillation state. When the permanent magnets of the transducer perform a reciprocating rotary motion in the resonance oscillation state, the angle difference between the direction of the velocity component of the permanent magnets in the direction perpendicular to the magnetic lines and the direction of the reaction force of the electromagnetic force is equal to the electrical angle difference. Due to $0.85f_0 < f_n < 1.05f_0$, such electrical angle difference is very small. In engineering applications, it can be considered approximately that the velocity component of the permanent magnets in the direction perpendicular to the magnetic lines and the reaction force of the electromagnetic force have the same direction, i.e., the electrical angle difference therebetween is zero, that is, if the electromagnetic force meets $F_e = NBI\, l\, \sin \omega t$, then when the permanent magnets of the transducer perform a reciprocating rotary motion, the velocity component of the permanent magnets in the direction perpendicular to the magnetic lines meets $\upsilon = \upsilon_M \sin \omega t$, where $\upsilon_M$ is the amplitude of the velocity component of the permanent magnets in the direction perpendicular to the magnetic lines.

According to the vibration principle, it is known that, in the resonance oscillation model where the driving frequency is constant, the amplitude of the motion of a forced vibrating object is proportional to the size of the driving force. In the present invention, the driving force acting upon the transducer of the forced vibrating object is derived from the electromagnetic force $F_e$ of the drive coil, $F_e = NBI\, l\, \sin \omega t$, where N, B, l and $\omega$ are constant values, I is the amplitude of current i, that is, the size of the current i is proportional to the size of the electromagnetic force $F_e$. Therefore, the motion amplitude of the cleaning elements can be controlled by controlling the size of i.

The electric cleaning care appliance of the present invention is often provided with various operation modes, such as cleaning mode, sensitive mode, whitening mode and the like. In the cleaning mode, the frequency $f_0$ of the current in the drive coil remains constant during each working period (e.g., 120 second). In the whitening mode, the frequencies $f_0$ of the current in the drive coil are two different frequencies changing alternately during each working period (e.g., 120 second). For example, the frequency of the current in the drive coil operates at a frequency of 260 HZ for 0.5 seconds, then operates at a frequency of 240 HZ for 0.5 seconds, then operates at a frequency of 260 HZ for 0.5 seconds, and then operates at a frequency of 240 HZ for 0.5 seconds, cycling in this order until the completion of the working period (e.g., 120 seconds). Apparently, in the present invention, the driving frequency of the current in the drive coil remains constant during a certain subdivided time period (e.g., the 0.5 seconds in the whitening mode). That is, during a certain subdivided time period of the operation of the electric cleaning care appliance, the current in the drive coil has a unique constant frequency. Therefore, the analysis about the relationship between the current and the motion amplitude of cleaning elements in the present invention is also suitable for the electric cleaning care appliance in which the current in the drive coil has a unique constant frequency at least during a certain subdivided time period.

The electric power $P_L$ on the drive coil can be derived from equation (4), $$\begin{cases} P_L = U_{LY} I_Y \cos\varphi \\ \cos\varphi = \dfrac{IR_L + NBl\upsilon_M}{\sqrt{(IR_L + NBl\upsilon_M)^2 + \omega^2 L^2 I^2}} \end{cases} \quad (6)$$

In this equation, $\upsilon_M$ is the amplitude of $\upsilon$, I is the amplitude of i, $U_{LY}$ is the effective value of the terminal voltage of the drive coil, and $I_Y$ is the effective value of i, Apparently, the electric power $P_L$ on the drive coil comprises the heat energy consumed by the DC resistance $R_L$ of the drive coil, the electromagnetic power (NB l $\upsilon$i) output to the transducer, and the idle work part (j$\omega$L$i^2$) stored in the inductive coil. Cos $\varphi$ in the equation (6) is a power factor. When cos $\varphi=1$, the electric power efficiency of the drive coil is the highest. It can be derived from cos $\varphi$ equation that, when the imaginary part j$\omega$L is zero, cos $\varphi=1$, and the smaller the j$\omega$L is, the closer the cos $\varphi$ is to 1.

Actually, the drive coil being an energy output part, its own inductance L can not be very low; otherwise it is impossible to output sufficient energy. At the same time, in order to achieve a reliable and efficient cleaning effect, the cleaning device is always required to operate at an operation frequency of 200-300 HZ, that is, $\omega$ is about between $400\pi$ to $600\pi$. Therefore, j$\omega$L can not be very small.

In order to decrease j$\omega$L, the present invention introduces capacitor(s) connected in series with the drive coil, so as to eliminate or enormously decrease the idle work part in the electric power $P_L$ on the drive coil, or alternatively, so as to control the size of power factor cos $\varphi$ by controlling the size of the idle work part in the electric power $P_L$ by means of capacitor(s).

Figure 6:
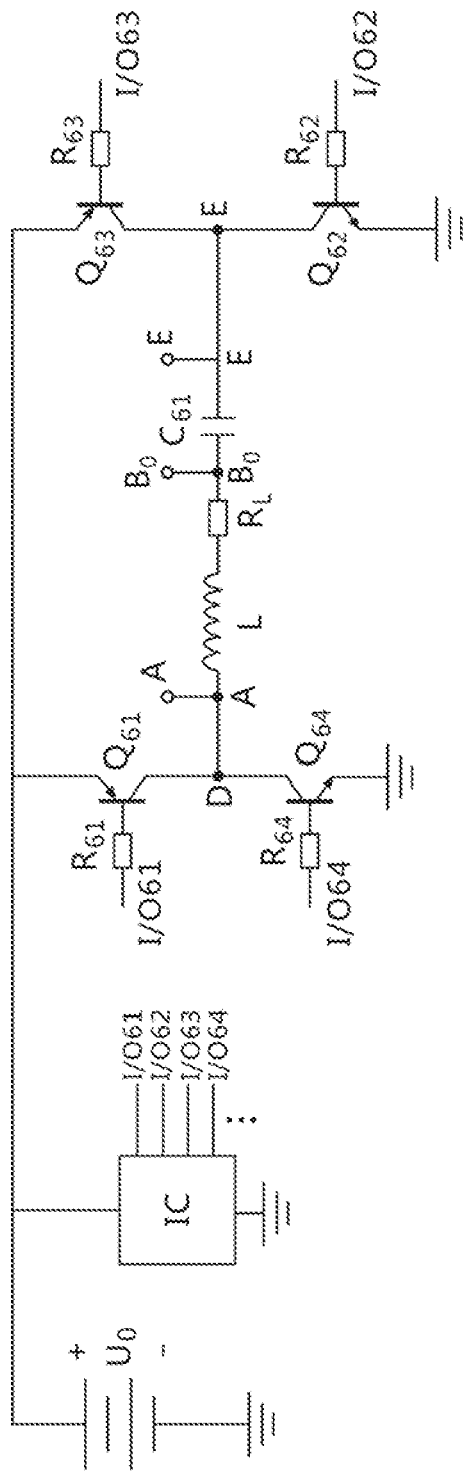
FIG. 6 is a control circuitry of a first embodiment of the present invention.

FIG. 6 is a control circuitry of a first embodiment of the present invention. As shown in FIG. 6, the capacitor bank comprises only one capacitor $C_{61}$. The capacitor $C_{61}$ and the drive coil are connected in series to the load ends of the H-bridge drive circuit, i.e., the capacitor $C_{61}$ and the drive coil are connected in series between the load nodes D and E of the H-bridge drive circuit. In this case, it is assumed that the natural frequency of the transducer, the cleaning element carrier and the cleaning elements is $f_n$, the driving frequency of the current in the drive coil is $f_0$, and make $f_0$ and $f_n$ satisfy the resonance oscillation condition $0.85f_0 < f_n < 1.05f_0$. For example, it is possible to set $f_0=260$ HZ, while according to the aforesaid Fourier series analysis, it's clear that, for the voltage rectangular wave with a frequency $f_0$ applied on the drive coil, only the electromagnetic force generated by the fundamental current can work together with the transducer, the cleaning element carrier and the cleaning elements with a natural frequency $f_n$ to generate resonance oscillation, while the third harmonic or higher-order harmonic of the voltage or current of the drive coil has its frequency far away from $f_n$, thereby the electromagnetic force generated by the third harmonic current or higher-order harmonic current in the drive coil cannot work together with the transducer, the cleaning element carrier and the cleaning elements with a natural frequency $f_n$ to generate a resonance oscillation effect. Therefore, its contribution to the motion amplitude of the cleaning elements is limited. That is, the electromagnetic force generated by the fundamental current with a frequency $f_0$ on the drive coil is the main driving force for driving the transducer, the cleaning carrier and the cleaning elements. The electrical angular speed w corresponding to the frequency $f_0$ is $2\pi f_0$. When $C_{61}$ satisfies the equation:

$$\frac{1}{\omega C_{61}} = \omega L, \ C_{61} = \frac{1}{\omega^2 L} = \frac{1}{4\pi^2 f_0^2 L},$$

as shown in FIG. 6, the voltage equation for the terminals AE is:

$$U_{AE} = iR_L + NBlv + j\left(\omega Li - i\frac{1}{\omega C_{61}}\right) \quad (7)$$

When $\frac{1}{\omega C_{61}} = \omega L$, $U_{AE} = iR_L + NBlv$

Apparently, the impedance of $C_{61}$ can effectively offset the impedance of the inductor. When $$\frac{1}{\omega C_{61}} = \omega L,$$

the drive coil is combined with the capacitor $C_{61}$ in such a way that the drive coil is purely resistive, thus the power factor $\cos \varphi$ of the circuit of the drive coil and the capacitor bank can be effectively improved, so that the $\cos \varphi$ is close or equal to 1 and thus the electrical efficiency of the drive coil is enormously increased. Absolutely, $1/\omega C_{61}$ is not necessary to be equal to $\omega L$. Apparently, by adjusting the size of the capacitance value of the capacitor $C_{61}$, different power factors $\cos \varphi$ can be achieved.

In this example, the analysis is only made to the case where the DC power supply applies a rectangular wave voltage with a frequency $f_0$ on the drive coil by means of a microchip processor. Similarly, the DC power supply can apply a sinusoidal wave or cosine wave voltage or a voltage of other wave shapes (e.g., triangular wave) with a frequency $f_0$ on the drive coil by means of a microchip processor or a multilevel coil. The analysis of the introduced capacitor $C_{61}$ connected in series with the drive coil is similar to the above analysis, and will not be repeated here.

In summary, the electric cleaning care appliance provided by the present invention has cleaning elements, a cleaning element carrier and a transducer capable of reciprocally rotating. The transducer is provided with elastic elements and permanent magnets. The cleaning elements, the cleaning element carrier and the transducer have a natural frequency $f_n$, and an alternating current with a frequency $f_0$ passes through the drive coil. The cleaning elements, the cleaning element carrier and the transducer perform reciprocating rotary motion in a resonance oscillation mode under the action of the electromagnetic force with a setting frequency $f_0$ generated on the drive coil. $f_n$ and $f_0$ satisfy: $0.85f_0 < f_n < 1.05f_0$. As the capacitor $C_{61}$ and the drive coil are connected in series to the load ends of the H-bridge drive circuit, the current flowing through the drive coil also flows through the capacitor, and the amplitude of the current flowing through the drive coil is equal to the amplitude of the current flowing through the capacitor.

Figure 7:
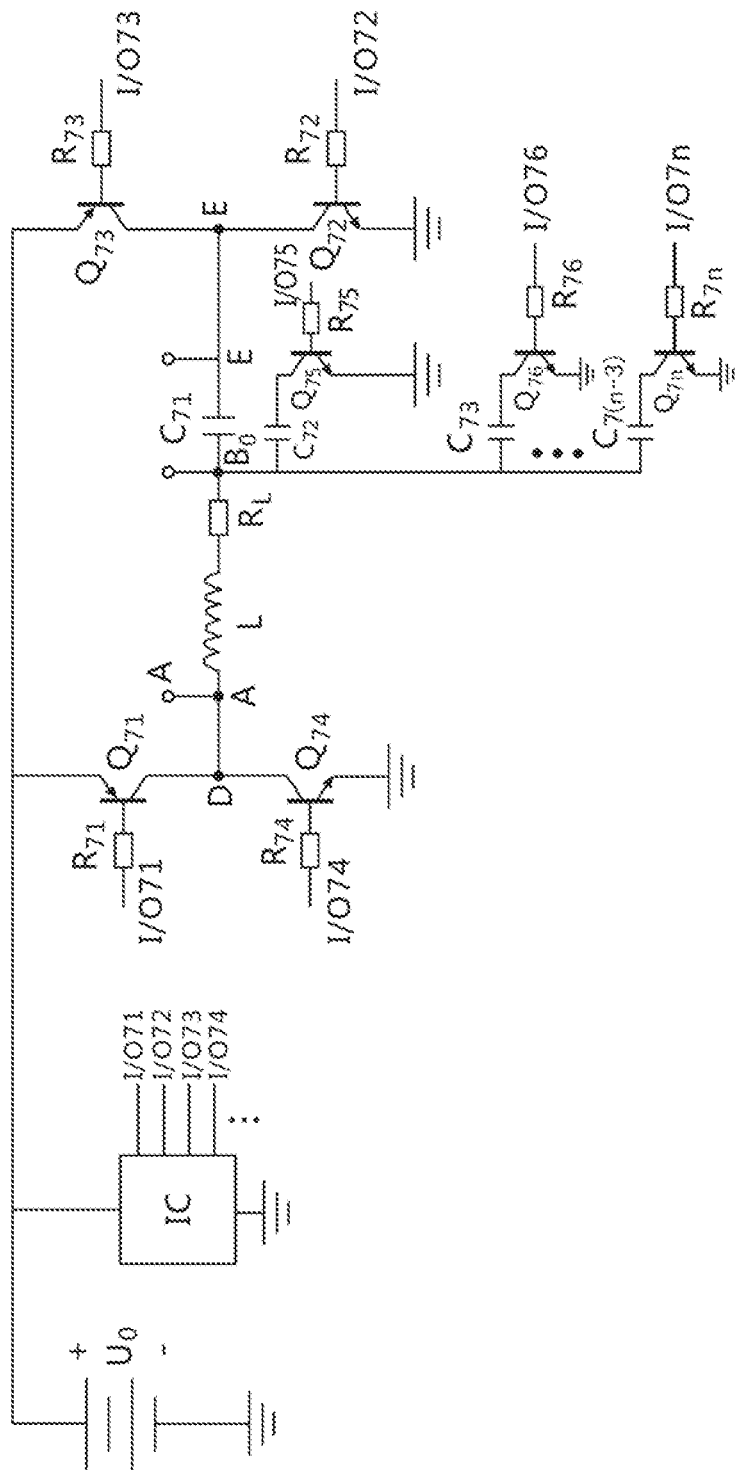
FIG. 7 is a control circuitry of a second embodiment of the present invention.

In a second embodiment, as shown in FIG. 7, a capacitor bank comprising at least two capacitors is introduced. This bank of capacitors is connected in series with the drive coil while the capacitance values of this bank of capacitors are controllable. In FIG. 7, the control circuit comprises a plurality of capacitors $C_{72}$, $C_{73}$, ..., $C_{7(n-3)}$ connected in series with the drive coil, and a plurality of transistors $Q_{75}$, $Q_{76}$, ..., $Q_{7n}$ connected in series with corresponding capacitors respectively. The branch in which the capacitor $C_{71}$ is combined with the transistors $Q_{73}$, $Q_{72}$ and is connected in series with the transistors $Q_{73}$, $Q_{72}$, the branch in which the capacitor $C_{72}$ is combined with the transistors $Q_{75}$ and is connected in series with the transistors $Q_{75}$, the branch in which the capacitor $C_{73}$ is combined with the transistors $Q_{76}$ and is connected in series with the transistor $Q_{76}$, and the branch in which the capacitor $C_{7(n-3)}$ is combined with the transistors $Q_{7n}$ and is connected in series with the transistor $Q_{7n}$ are in parallel with each other. During the positive half cycle or the negative half cycle or the whole cycle of the current of the drive coil, the transistor Q and the drive coil of at least one of the branches are kept always on or off synchronously, hence the capacitor and the drive coil in this branch are kept always connected or disconnected synchronously during the cycle of the current, thus ensuring that the drive coil will not occur additional on-off caused by the connection of the capacitor connected in series, to avoid the generation of additional electromagnetic interference due to the additional on-off of the drive coil. For example, in FIG. 7, during the overall cycle of the current of the drive coil, $C_{71}$ is kept always connected or disconnected synchronously with the drive coil. The microchip processor controls whether other capacitors are connected by means of output level of the corresponding I/O interfaces. For example, the microchip processor controls I/O71, I/O74 so that I/O71, I/O74 remain at a low level; the microchip processor controls I/O72, I/O73 so that I/O72, I/O73 remain at a high level; the microchip processor controls I/O75 so that I/O75 remains at a low level, then the transistor $Q_{75}$ is not turned on, while the microchip processor controls I/Os associated with other capacitors, such as I/O72, I/O76, ..., I/O7n, so that corresponding transistors, such as $Q_{72}$, $Q_{76}$, ..., $Q_{7n}$ are turned on. By this time, all of the other capacitors of the capacitor bank are connected in parallel except the capacitor $C_{72}$, and the equivalent capacitance of the capacitor bank is $$C_{e7h} = \sum_{i=1}^{n-3} C_{7i} - C_{72}.$$

Apparently, by means of the above capacitor bank, it is possible to achieve a controllable capacitance value when $Q_{71}$, $Q_{72}$ are turned on, i.e. during the positive half cycle of the current of the drive coil, while $Q_{76}$, ..., $Q_{7n}$ are turned on simultaneously. In the above capacitor bank, the capacitors in the on state are connected in parallel with each other, and the capacitors in the on state are connected in series with the drive coil. The current flowing through the drive coil also flows through the transistor in the on state and corresponding capacitors, and the sum of the currents flowing through all of the transistors in the on state and corresponding capacitors is equal to the current flowing through the drive coil. Since the voltage-drop of the transistors $Q_{71}$, $Q_{72}$, $Q_{73}$, ..., $Q_{7n}$ on the path along which the current of the drive coil flows is very low and can be ignored, the size of the absolute value of voltage amplitude between points A and E in FIG. 7 is approximately equal to the output voltage $U_0$ of DC power supply. In this example, when $Q_{73}$, $Q_{74}$ are turned on, i.e., during the negative half cycle of the current of the drive coil, all of the other capacitors $C_{72}$, $C_{73}$, ..., $C_{7(n-3)}$ except $C_{71}$ are disconnected by $Q_{75}$, $Q_{76}$, ..., $Q_{7n}$, i.e., the capacitors $C_{72}$, $C_{73}$, ..., $C_{7(n-3)}$ are disconnected from the drive coil, then during the overall current cycle of the drive coil $$C_e = \left(\sum_{i=1}^{n-3} C_{7i} - C_{72}\right)/2 + C_{71}/2,$$

the current flowing through the drive coil is:

$$\begin{cases} i = \dfrac{\dfrac{4}{\pi}U_0 \sin\omega t - NBlv}{R_L + j\left(\omega L - \dfrac{1}{\omega C_e}\right)} \\ I = \dfrac{\dfrac{4}{\pi}U_0 - NBlv_M}{\sqrt{(R_L)^2 + \left(\omega L - \dfrac{1}{\omega C_e}\right)^2}} \end{cases} \quad \text{(8)}$$

$I$ is the amplitude of $i$

It is know from equation (8) that $C_e$ in this equation is the equivalent capacitance value of the capacitor bank, i.e., the sum of the capacitance values of all the capacitors in the on state. When $(\omega L - 1/\omega C_e)$ is large, the current amplitude I of the drive coil tends to be zero. When $(\omega L - 1/\omega C_e) = 0$, the current amplitude I of the drive coil is equal to $$\dfrac{\dfrac{4}{\pi}U_0 - NBlv_M}{R_L}$$

In this example, the electromagnetic force between the drive coil and the transducer could bring the transducer, the cleaning element carrier and the cleaning elements into a resonance oscillation state. If the electromagnetic force meets $F_e = NBI\,l\sin\omega t$, the velocity at which the permanent magnets of the transducer reciprocate meets $v = v_M \sin \omega t$, and the permanent magnets of the transducer make a simple harmonic vibration under the action of the electromagnetic force. The velocity $v_M$ at which the permanent magnets of the transducer reciprocate is proportional to the size of the electromagnetic force $F_e$. Due to NB l in this case being a constant value, when the permanent magnets of the transducer make a reciprocating rotary motion, the amplitude $v_M$ of the velocity component of the permanent magnets in the direction perpendicular to the magnetic lines is proportional to the size of the current in the drive coil. Given $v_M = ZI$, here Z is the change rate of the amplitude of the velocity component of the permanent magnets in the direction perpendicular to the magnetic lines with respect to the amplitude of the current in the drive coil, which can be obtained experimentally. When $(\omega L - 1/\omega C_e)$ is large, the current amplitude I of the drive coil tends to be zero, and the motion amplitude of the cleaning elements tends to be zero. When $(\omega L - 1/\omega C_e) = 0$, the current amplitude I of the drive coil is equal to $$\dfrac{\dfrac{4}{\pi}U_0}{R_L + ZNBl}.$$

The motion amplitude of the cleaning elements tends to be maximum, and the motion amplitude of the cleaning elements is proportional to $$\dfrac{\dfrac{4}{\pi}U_0}{R_L + ZNBl}.$$

Here, the drive coil and the capacitor bank are purely resistive, the power factor $\cos\varphi$ of the circuit of the drive coil and the capacitor bank equals to 1, and the electrical efficiency of the circuit is the highest. Apparently, with the capacitor bank, the capacitance value of which is controllable, being connected in series in the circuit, it is possible to adjust the amplitude I of the current flowing through the drive coil from near zero to $$\dfrac{\dfrac{4}{\pi}U_0}{R_L + ZNBl},$$

in such a way that the motion amplitude of the cleaning elements is adjusted from near zero to the maximum. It is self-evident that a low current corresponds to a small motion amplitude of the cleaning elements. The lower the current is, the less the heat energy consumed on the DC resistance $R_L$ of the drive coil. In this case, a capacitor bank, the capacitance value of which is controllable, is introduced, therefore, by varying the equivalent capacitance value of the capacitor bank connected in series with the drive coil, it is possible to adjust the power factor of the circuit of the drive coil and the capacitor bank, and the amplitude of the current flowing through the drive coil in a controllable way.

Since the frequency of the current flowing through the drive coil during a certain subdivision time period of the operation of the electric cleaning care appliance is a unique constant frequency, the amplitude of the rotary motion of the transducer, the cleaning element carrier and the cleaning elements of the cleaning care appliance in the present invention is proportional to the amplitude of the current flowing through the drive coil. In this case, there are provided a capacitor bank composed of at least two capacitors connected in parallel with each other (parallel capacitor bank), wherein at least one capacitor (e.g., a first capacitor) is always kept connected or disconnected synchronously with the drive coil. The connection of a portion of or all of the remained capacitors of the capacitor bank is controlled by means of a microchip processor IC, and these capacitors connected in parallel with each other are connected in series with the drive coil, so that the current flowing through the drive coil also flows through all of the connected capacitors connected in parallel with each other, thus the sum of the currents flowing through all of the connected capacitors is equal to the current flowing through the drive coil. By connecting in series a capacitor bank with different equivalent capacitances in the circuit of the drive coil in a controllable way, the current flowing through the drive coil can controllably limited to a value from approximately zero to $$\frac{\frac{4}{\pi}U_0}{R_L + ZNBl},$$

and the size of the motion amplitude of the cleaning elements can be controlled. Still further, by connecting in series a capacitor bank with different equivalent capacitances in the circuit of the drive coil in a controllable way, the motion amplitude of the cleaning elements can be controllably limited to a value ranging from approximately zero to the maximal amplitude to which the system corresponds. When the drive coil and the equivalent capacitance connected in series are purely resistive $$\left(\text{i.e., } \frac{1}{\omega C_e} = \omega L\right),$$

the maximum motion amplitude, to which the system corresponds, occurs.

Figure 8:
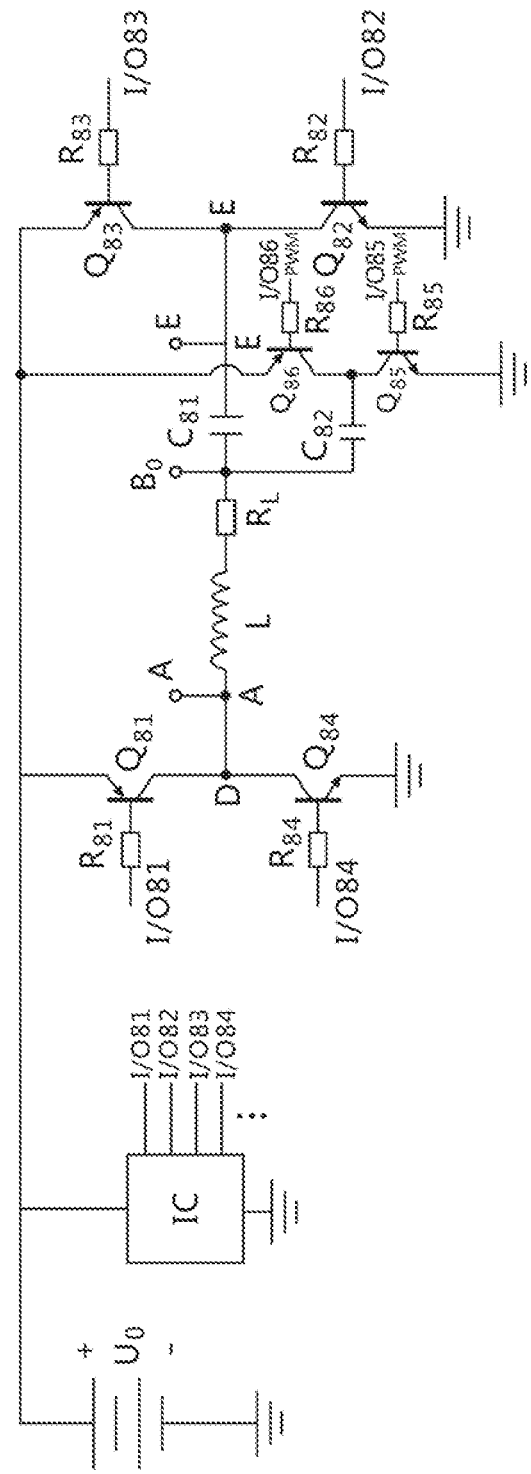
FIG. 8 is a control circuitry of a third embodiment of the present invention.
Figure 9:
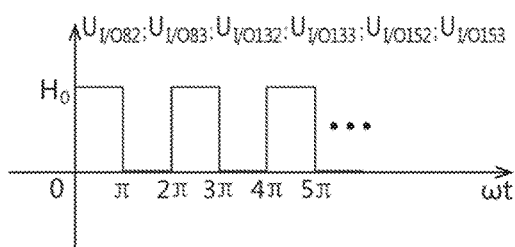
FIG. 9 is a voltage timing diagram of I/O82, I/O83 (FIG. 8), I/O132, I/O133 (FIG. 13), and I/O152, I/O153 (FIG. 15) in the IC circuit IC.
Figure 10:
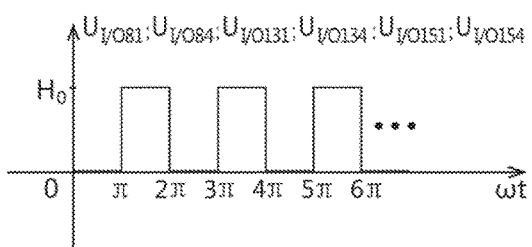
FIG. 10 is a voltage timing diagram of I/O81, I/O84 (FIG. 8), I/O131, I/O134 (FIG. 13), and I/O151, I/O154 (FIG. 15) in the IC circuit.

FIG. 8 presents a control circuit of a third embodiment of the present invention. The difference between FIGS. 8 and 7 is that the capacitor bank in FIG. 8 comprises two capacitors $C_{81}$, $C_{82}$ connected in parallel. The branch in which a first capacitor $C_{81}$ is combined with the transistors $Q_{82}$ and $Q_{83}$ and is connected in series with the transistors $Q_{82}$ and $Q_{83}$ and the branch in which a second capacitor $C_{82}$ is combined with the transistors $Q_{85}$, $Q_{86}$, are connected in parallel with each other. The drive coil is connected in series with the capacitor bank. The first capacitor $C_{81}$ is always kept connected or disconnected synchronously with the drive coil. The second capacitor $C_{82}$ is connected in parallel with the first capacitor $C_{81}$ by the on-off control of the corresponding transistors $Q_{85}$ and $Q_{86}$. The on or off of the transistors $Q_{85}$ and $Q_{86}$ is controlled by corresponding I/O85 and I/O86 of the microchip processor IC.

Figure 11:
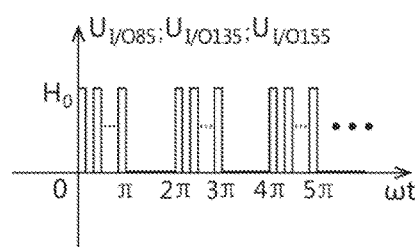
FIG. 11 is a voltage timing diagram of I/O85 (FIG. 8), I/O135 (FIG. 13), and I/O155 (FIG. 15) in the IC circuit IC.

FIGS. 9, 10, 11 and 12 are electrical level timing diagram of I/O81, I/O82, I/O83, I/O84, I/O85 and I/O86. When ωt is in the interval of 0-π, I/O82 and I/O83 are at high level, I/O81 and I/O84 are at low level, I/O85 is a level output of PWM mode, and I/O86 is at high level. When ωt is in the interval of π-2π, I/O82 and I/O83 are at low level, I/O81 and I/O84 are at high level, I/O85 is at low level, and I/O86 is a level output of PWM mode. When ωt is in the interval of 0-π, according to FIGS. 8, 9, 10, 11 and 12, the transistors $Q_{81}$, and $Q_{82}$ are turned on, while transistor $Q_{85}$ is turned on or off according to PWM mode, current i from the DC power supply flows from the point A in FIG. 8 to point $B_0$ via the drive coil. In the PWM mode, when the transistor $Q_{85}$ is in the on state and the transistor $Q_{86}$ is in the off state, a part of the current i flows through the capacitor $C_{81}$ and the transistor $Q_{82}$ toward the DC power supply, another part of the current i flows through the capacitor $C_{82}$ and the transistor $Q_{85}$ and back into the DC power supply, and the size of the current flowing through the drive coil is equal to the sum of the currents flowing through the capacitors $C_{81}$ and $C_{82}$. By this time, the drive coil is connected in series with the two parallel capacitors $C_{81}$ and $C_{82}$. Due to the equivalent resistance between the collector and emitter of the transistor being small, the equivalent resistance of the transistor can be ignored, then the equivalent impedance of the drive coil and the capacitor bank is $$R_L + j\left[L - \frac{1}{\omega(C_{81} + C_{82})}\right],$$

i.e., the equivalent capacitance value $C_e$ of the capacitor bank is the sum of the capacitances of the capacitors $C_{81}$ and $C_{82}$. When the transistor $Q_{85}$ is in the off state under the PWM mode and the transistor $Q_{86}$ is also in the off state, all of the current i from the DC power supply flowing through the drive coil flows through the capacitor $C_{81}$ and the transistor $Q_{82}$ and back into the DC power supply. By this time, the drive coil is connected in series with the capacitor $C_{81}$. Similarly, the equivalent resistance of the transistor is ignored, then the equivalent impedance of the drive coil and the capacitor bank is $$R_L + j\left(\omega L - \frac{1}{\omega C_{81}}\right),$$

i.e., the equivalent capacitance value of the capacitor bank is the capacitance value of the capacitor $C_{81}$. If assuming y is the duty cycle of PWM, for example as shown in FIG. 11, when 0<ωt<π, $y_1$ refers to the ratio of the time for high level to the total time $$\frac{\pi}{\omega}$$

in PWM mode. Apparently, when 0<ωt<π, the mean equivalent capacitance value of the above capacitor bank is $C_{emh1}=C_{81}+y_1C_{82}$. Apparently, the capacitors $C_{81}$ and $C_{81}$ will not additionally increase the on-off of the drive coil, so that the continuity of the current in the drive coil can be maintained.

Figure 12:
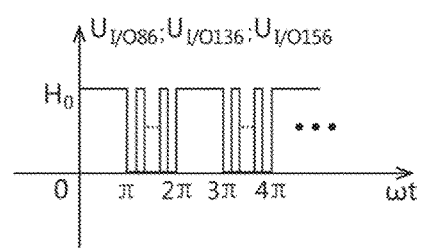
FIG. 12 is a voltage timing diagram of I/O86 (FIG. 8), I/O136 (FIG. 13), and I/O156 (FIG. 15) in the IC circuit.

When π<ωt<2π, the transistors $Q_{83}$, $Q_{84}$ are turned on, the transistors $Q_{81}$, $Q_{82}$, $Q_{85}$ are turned off, the transistor $Q_{86}$ is turned on in the PWM mode as shown in FIG. 12, the circuit analysis is similar to that of 0<ωt<π, and will not be repeated here. When π<ωt<2π, as shown in FIG. 12, $y_2$ refers to the ratio of the time for low level to the total time $$\frac{\pi}{\omega}$$

in PWM mode. When π<ωt<2π, the mean equivalent capacitance value of the capacitor bank is $C_{emh2}=C_{81}+y_2C_{82}$. Apparently, the capacitors $C_{81}$ and $C_{82}$ will not additionally increase the on-off of the drive coil; therefore, the continuity of the current in the drive coil can be maintained. Therefore, during the entire time period of the operation of the circuit, the mean equivalent capacitance value of the parallel capacitor bank is $$C_{emp} = \frac{C_{emh1} + C_{emh2}}{2} = C_{81} + \frac{y_1 + y_2}{2}C_{82}.$$

Apparently, the capacitors $C_{81}$ and $C_{82}$ will not additionally increase the on-off of the drive coil; therefore, the continuity of the current in the drive coil can be maintained.

In the present invention, the PWM duty cycles $y_1$ and $y_2$ of I/O85, I/O86 are controlled by means of a microchip processor IC, thereby it is possible to control the mean equivalent capacitance value $C_{emh}$ of the parallel capacitor bank connected in series with the drive coil. Here, by controlling the mean equivalent capacitance value $C_{emh}$, the size and phase angle of the impedance of the drive coil and the parallel capacitor bank can be controlled, and thus the size of the current flowing through the drive coil and the size of the power factor of the circuit of the drive coil and the parallel capacitor bank can be controlled. According to the present invention, a parallel capacitor bank, the mean equivalent capacitance of which is controllable, is creatively connected in series with the drive coil, so that it is possible to control the size of the current flowing through the drive coil and the electric power factor cos φ of the circuit of the drive coil and the capacitor bank. Furthermore, the capacitor or capacitor bank connected in series with the drive coil according to the present invention will not additionally increase the on-off of the drive coil.

Figure 13:
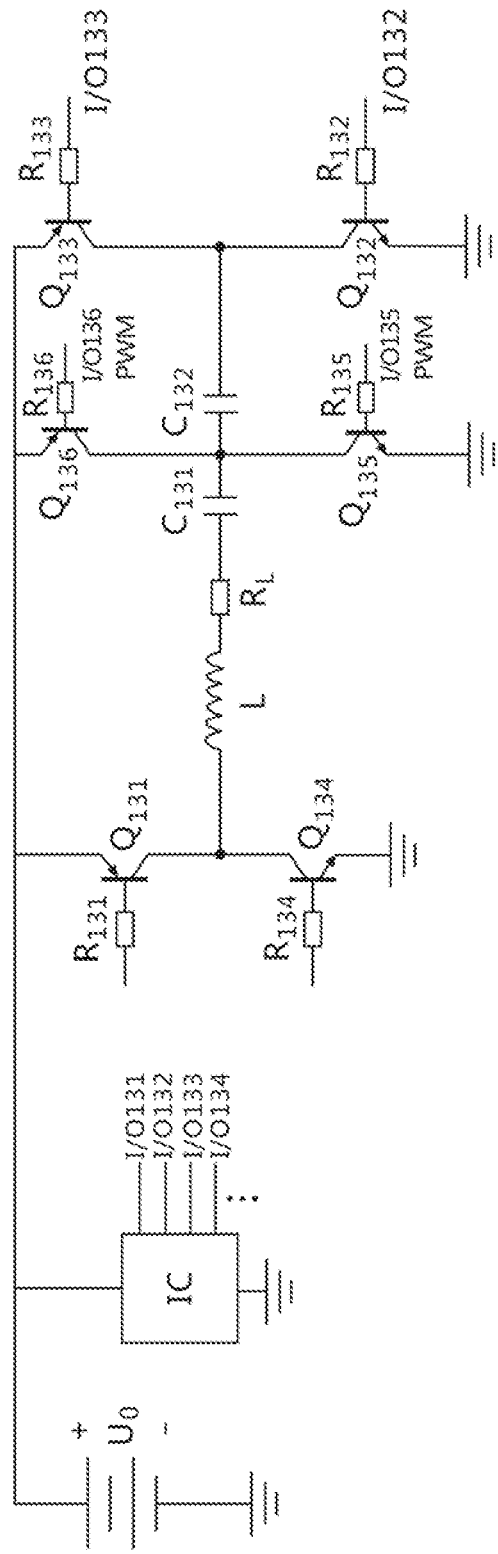
FIG. 13 is a control circuitry of a fourth embodiment of the present invention.

FIG. 13 presents a control circuit of a fourth embodiment of the present invention. The difference between FIGS. 13 and 8 is that the capacitor bank in FIG. 13 comprises two capacitors $C_{131}$, $C_{132}$ in series. The circuit in FIG. 13 can be specifically analyzed in a similar way, and will not be repeated here. The feature of the circuit in FIG. 13 is analyzed only in a simple way, as shown in FIGS. 13, 9, 10, 11 and 12, for example, during a certain time period (0<ωt<π), the microchip processor IC turns on the transistors $Q_{131}$, $Q_{132}$, turns off the transistors $Q_{133}$, $Q_{134}$, $Q_{136}$, and turns on the transistor $Q_{135}$ in a PWM mode. When the transistor $Q_{135}$ is in the off state under PWM mode, the first capacitor $C_{131}$ and the second capacitor $C_{132}$ are connected in series to form a tandem capacitor bank $C_{131}$, $C_{132}$, here the equivalent capacitance value of the tandem capacitor bank is $$\frac{C_{131} C_{132}}{C_{131} + C_{132}}.$$

When the transistor $Q_{135}$ is in the on state under PWM mode, the equivalent capacitance value of the tandem capacitor bank is equal to the capacitance value of $C_{131}$. In a similar way, given that $y_3$ refers to the ratio of the time for high level to the total time π/ω in the PWM mode, apparently, when 0<ωt<π, the mean equivalent capacitance value of the above tandem capacitor bank is $$C_{em3h1} = C_{131} - y_3 \frac{C_{131}^2}{C_{131} + C_{132}}.$$

During another time period (π<ωt<2π), the microchip processor IC turns on the transistors $Q_{133}$, $Q_{134}$, turns off the transistors $Q_{131}$, $Q_{132}$, $Q_{135}$, and turns on the transistor $Q_{136}$ in a PWM mode. When the transistor $Q_{136}$ is in the off state under PWM mode, the first capacitor $C_{131}$ and the second capacitor $C_{132}$ are connected in series to form a tandem capacitor bank, here the equivalent capacitance value of such a tandem capacitor bank is $$\frac{C_{131} C_{132}}{C_{131} + C_{132}}.$$

When the transistor $Q_{136}$ is in the on state under PWM mode, the equivalent capacitance value of the capacitor bank is equal to the capacitance value of capacitor $C_{131}$. In a similar way, given that $y_4$ refers to the ratio of the time for low level to the total time $$\frac{\pi}{\omega}$$

in the PWM mode, apparently, when π<ωt<2π, the mean equivalent capacitance value of the above capacitor bank is $$C_{em3h2} = C_{131} - y_4 \frac{C_{131}^2}{C_{131} + C_{132}}.$$

Therefore, during the entire time period for the operation of the circuit, the mean equivalent capacitance value of the capacitor bank is $$C_{ems} = \frac{C_{emh1} + C_{emh2}}{2} = C_{131} - \frac{y_3 + y_4}{2} \frac{C_{131}^2}{C_{131} + C_{132}}.$$

In this case, the microchip processor IC controls the PWM duty cycles $y_3$ and $y_4$ of I/O135, I/O136, thereby controls the mean equivalent capacitance value $C_{ems}$ of the tandem capacitor bank connected in series with the drive coil, the size and phase angle of the impedance of the drive coil and the tandem capacitor bank are controlled by means of a controllable mean equivalent capacitance $C_{ems}$, thereby the size of the current flowing through the drive coil and the size of the power factor of the circuit of the drive coil and the tandem capacitor bank are controlled. Thus, according to the present invention, the drive coil is creatively connected in series with a capacitor bank with a controllable mean equivalent capacitance value, so that the size of the current flowing through the drive coil and the electric power factor cos φ of the circuit of the drive coil and the capacitor bank can be controlled.

Figure 14:
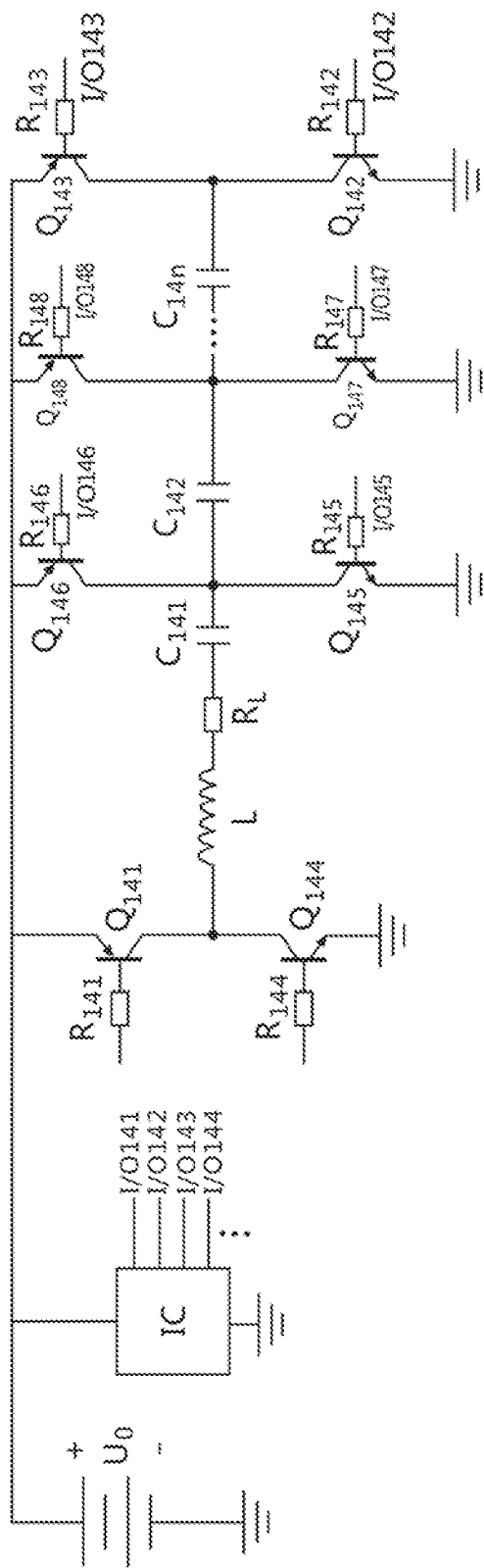
FIG. 14 is a control circuitry of a fifth embodiment of the present invention.

Similarly, a plurality of capacitor banks connected in series with each other can be controlled by the microchip processor IC, as shown in a control circuitry of a fifth embodiment in FIG. 14 of the present invention. The difference between FIGS. 14 and 13 is that the capacitor bank in FIG. 14 is composed of more than two tandem capacitors $C_{141}$-$C_{146}$. Its circuit analysis is similar to that for FIGS. 7, 8 and 13 in this description, and will not be repeated here.

Figure 15:
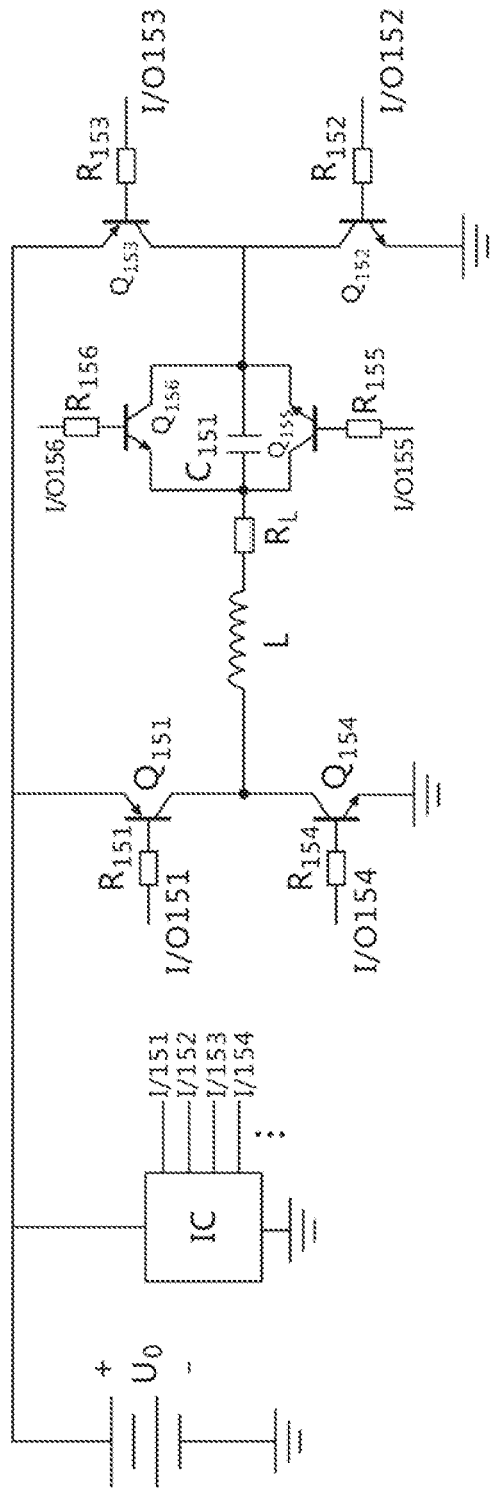
FIG. 15 is a control circuitry of a sixth embodiment of the present invention.

In the above five embodiments, at least one capacitor is always kept on or off synchronously with the drive coil. Of course, it may not be necessary to always keep at least one capacitor to be on or off synchronously with the drive coil. Similarly, the size and phase angle of the impedance of the drive coil and the capacitor bank can be controlled by controlling the mean equivalent capacitance value $C_e$ of the capacitors or capacitor bank connected in series with the drive coil, thus the size of the current flowing through the drive coil and the size of the power factor of the circuit of the drive coil and the capacitor bank are controlled. As shown in a sixth embodiment of the present invention in FIG. 15.

As shown in FIGS. 9, 10, 11, 12, and 15, for example, during a certain time period ($0<\omega t<\pi$), the microchip processor IC turns on the transistors $Q_{151}$, $Q_{152}$, turns off the transistors $Q_{153}$, $Q_{154}$, $Q_{156}$, and turns on the transistor $Q_{155}$ in PWM mode. When the transistor $Q_{155}$ is in the off state under PWM mode, the capacitor $C_{151}$ is connected in series with the drive coil, and the equivalent capacitance value of the capacitor bank is equal to the capacitance value of capacitor $C_{151}$. When the transistor $Q_{155}$ is in the on state under PWM mode, the capacitor $C_{151}$ is short-circuited by the transistor $Q_{155}$, and the equivalent capacitance value of the capacitor bank is zero. In a similar way, given that $y_3$ refers to the ratio of the time for high level to the total time $$\frac{\pi}{\omega}$$

in the PWM mode, apparently, when $0<\omega t<\pi$, the mean equivalent capacitance value of the above capacitor bank is $C_{e5h1}=(1-y_3)C_{151}$, while during another time period ($\pi<\omega t<2\pi$), the microchip processor IC turns on the transistors $Q_{153}$, $Q_{154}$, turns off the transistors $Q_{151}$, $Q_{152}$, $Q_{155}$, and turns on the transistor $Q_{156}$ in a PWM mode. When the transistor $Q_{156}$ is in the off state under PWM mode, the capacitor $C_{151}$ is connected in series with the drive coil, and the equivalent capacitance value of the capacitor bank is equal to the capacitance value of capacitor $C_{151}$. When the transistor $Q_{156}$ is in the on state under PWM mode, the capacitor $C_{151}$ is short-circuited by the transistor $Q_{156}$, and the equivalent capacitance value of the capacitor bank is zero. In a similar way, given that $y_4$ refers to the ratio of the time for low level to the total time $$\frac{\pi}{\omega}$$

in the PWM mode, apparently, when $\pi<\omega t<2\pi$, the mean equivalent capacitance value of the above capacitor bank is $C_{e5h2}=y_4 C_{151}$. Therefore, during the entire current cycle of the drive coil, the mean equivalent capacitance value of the capacitor bank is $$C_{e5} = \frac{C_{e5h1} + C_{e5h2}}{2} = (1 - y_3 + y_4)C_{151}/2.$$

In this case, the microchip processor IC controls the PWM duty cycles $y_3$ and $y_4$ of I/O135, I/O136, thereby the mean equivalent capacitance value $C_{e5}=(1-y_3+y_4) C_{151}/2$ of the capacitor bank connected in series with the drive coil can be controlled. Here, the size and phase angle of the impedance of the drive coil and the capacitor bank are controlled by means of the controllable mean equivalent capacitance $C_{e5}$, thereby the size of the current flowing through the drive coil and the size of the power factor of the circuit of the drive coil and the capacitor bank are controlled. Thus, according to the present invention, the drive coil is creatively connected in series with a capacitor bank with a controllable mean equivalent capacitance value, so that the size of the current flowing through the drive coil and the electric power factor cos φ of the circuit of the drive coil and the capacitor bank can be controlled. Moreover, in the present invention, the capacitors or capacitor bank connected in series with the drive coil will not additionally increase the on-off of the drive coil. Obviously, the above description is only illustrative, those skilled in the art can also make various changes and modifications thereto without departing from the scope of the invention as defined by the claims. These changes and modifications should fall into the scope of the present invention defined by the claims.

What is claimed is:

1. An adjustable circuit for a personal electric cleaning care appliance, the cleaning care appliance comprises a power supply portion for supplying power to various parts of the cleaning care appliance, a control portion for controlling various operation modes of the cleaning care appliance, a trigger portion for turning on or off the operation of the cleaning care appliance, and a driver for converting input electrical energy into a mechanical energy output; the power supply portion comprises an H-bridge drive circuit composed of transistors; the driver comprises a transducer, a drive coil, and an iron core of the drive coil located within the drive coil, the transducer is provided with elastic elements and permanent magnets thereon, a drive shaft of the transducer is equipped with a cleaning element carrier and cleaning elements;

the adjustable circuit comprises a microchip processor (IC) and the H-bridge drive circuit; wherein a driving frequency generated by the H-bridge drive circuit is set to $f_0$, when the drive coil is fed with an alternating current i, the current in the drive coil contains a sinusoid current part with a frequency of $f_0$, the cleaning elements, the cleaning element carrier and the transducer make a reciprocating rotary motion in a resonance oscillation mode under the action of the electromagnetic force with a setting frequency $f_0$ generated by the drive coil; the cleaning elements, the cleaning element carrier and the transducer have a natural frequency $f_n$, $f_n$ satisfies: $0.85f_0<f_n<1.05f_0$; during a certain subdivision time period of the operation of the electric cleaning care appliance corresponding to an operating mode, the current in the drive coil has a unique constant frequency; wherein a capacitor bank and a drive coil in series with the capacitor bank are connected at load ends of the H-bridge drive circuit, at least a part of the capacitors of the capacitor bank is controlled to be connected in series with the drive coil or disconnected from the drive coil through an interface (I/O) of the programmable microchip processor (IC), as a result, a capacitance of the connected capacitor(s) can be controlled so that the current flowing through the drive coil is controllably limited to a value between approximate zero to $$\frac{\frac{4}{\pi}U_0}{R_L + ZNBl},$$

and thereby the size of motion amplitude of the cleaning elements can be controlled, in the equation, $U_0$ is an output voltage of the power supply, $R_L$ is a DC resistance of the drive coil, Z is a change rate of the amplitude of a velocity component of the permanent magnets perpendicular to the direction of the magnetic lines with respect to the amplitude of the current of the drive coil, Z is obtained experimentally, N is the number of turns of the drive coil cut by the magnetic lines, B is a magnetic field density at a conductor of the drive coil, and l is an effective length of the coil conductor cut by the magnetic lines;

wherein the capacitor bank comprises a plurality of capacitors ($C_{72}$, $C_{73}$, ... $C_{7(n-3)}$) which are connected in series with corresponding transistors ($Q_{75}$, $Q_{76}$, ... $Q_{7n}$) respectively to form branches, these branches are connected in parallel with each other and in series with the drive coil, during a positive half cycle or a negative half cycle or a whole cycle of the current of the drive coil, the transistor (Q) and the drive coil in at least one branch are kept always turned on or off synchronously.

2. The adjustable circuit for a personal electric cleaning care appliance according to claim 1, wherein an equivalent capacitance value of the capacitor bank is selected so that a loop resistance of the drive coil and the capacitor bank is purely resistive.

3. The adjustable circuit for a personal electric cleaning care appliance according to claim 1, wherein the capacitor bank comprises at least two capacitors ($C_{72}$, $C_{73}$, ... $C_{7(n-3)}$) connected in parallel with each other.

* * * * *